United States Patent [19]

Cetenko et al.

[11] Patent Number: 4,824,958

[45] Date of Patent: Apr. 25, 1989

[54] PROCESS FOR THE PREPARATION OF N-1H-TETRAZOL-5-YL-2-PYRROLE CARBOXAMIDES

[75] Inventors: Wiaczeslaw A. Cetenko; David T. Connor, both of Ann Arbor; Michael D. Mullican, Ypsilanti; Roderick J. Sorenson, Ann Arbor, all of Mich.

[73] Assignee: Warner-Lambert Company, Morris Plains, N.J.

[21] Appl. No.: 155,784

[22] Filed: Feb. 16, 1988

Related U.S. Application Data

[60] Division of Ser. No. 27,453, Mar. 18, 1987, Pat. No. 4,748,183, which is a continuation-in-part of Ser. No. 874,309, Jun. 13, 1986, abandoned.

[51] Int. Cl.$^4$ .................. C07D 257/06; C07D 207/12
[52] U.S. Cl. ..................................... 548/251; 548/532
[58] Field of Search ............................... 548/251, 532

[56] References Cited

FOREIGN PATENT DOCUMENTS

| 45-33649 | 10/1970 | Japan | 548/532 |
| 0246384 | 12/1985 | Japan | 548/251 |
| 1189264 | 8/1986 | Japan | 548/532 |

*Primary Examiner*—David B. Springer
*Attorney, Agent, or Firm*—Joan Thierstein

[57] ABSTRACT

The present invention is for compounds having the formula of N-1H-tetrazol-5-yl-2-thiophenecarboxamides, N-1H-tetrazol-5-yl-2-pyrrolecarboxamides, N-1H-tetrazol-5-yl-2-furancarboxamides or analogs of each of the carboxamides. The compounds are useful for the treatment of allergic or inflammatory conditions or diseases. Thus, pharmaceutical compositions and methods of use are also the invention. Processes of preparation for the compounds are also the invention.

2 Claims, No Drawings

PROCESS FOR THE PREPARATION OF N-1H-TETRAZOL-5-YL-2-PYRROLE CARBOXAMIDES

This is a divisional of U.S. application Ser. No. 027,453 filed 3/18/87 now U.S. Pat. No. 4,748,183 which is a continuation-in-part of U.S. application Ser. No. 874,309 filed 6/13/86, now abandoned.

BACKGROUND OF THE INVENTION

The present invention is for novel carboxamides of two ring systems in the same compound not previously known. One of the rings in each compound is a tetrazole. The other is thiophene, pyrrole or furan. The carboxamides have activity useful for treating allergic and inflammatory conditions or diseases. Thus, the invention herein also relates to pharmaceutical compositions and methods of use therefor.

Previously known compounds having a tetrazolyl substituent include benzothiophenes and benzofurans disclosed in copending application U.S. Ser. No. 790,664, filed Oct. 28, 1989 which is a continuation-in-part of U.S. Ser. No. 680,108 filed Dec. 10, 1984. The compounds of these applications prevent the release of mediators including histamine and leukotrienes from basophils and mast cells, and prevent respiratory burst of neutrophils and thus also have antiallergic and immunoinflammatory activity. European Patent Application No. 0146243 discloses benzofurans and benzothiophenes of which selected compounds include a tetrazolyl substituent as well. The EP No. 0146243 discloses 5-lipoxygenase activity.

Thus, the known compounds described above do not include the combination of ring systems now the present invention.

SUMMARY OF THE INVENTION

The present invention are compounds of the formula (I)

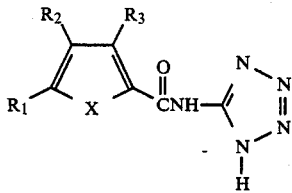

and pharmaceutically acceptable salts thereof, wherein $R_1$, $R_2$ and $R_3$ may be the same or different and are (i) hydrogen; (ii) lower alkyl; (iii) lower alkoxy; (iv) phenyl unsubstituted or substituted with of from one to five, preferably from one to three, substituents comprising one or more of each of halogen, trifluoromethyl, lower alkyl, hydroxy, lower alkoxy, nitro, amino, mono lower alkylamino, or dilower alkylamino; (v) halogen; (vi) trifluoromethyl; (vii) hydroxy; (viii) amino, (ix) mono lower alkylamino; (x) dilower alkylamino; (xi) nitro; (xii) mercapto; (xiii) lower alkylthio; (xiv) lower alkylsulfinyl; or (xv) lower alkylsulfonyl;

X is O, $S(O)_{0-2}$ or $NR_4$ wherein $R_4$ is hydrogen; lower alkyl; phenyl unsubstituted or substituted by of from one to five, preferably from one to three, substituents comprising one or more of each of halogen, trifluoromethyl, lower alkyl, hydroxy, lower alkoxy, nitro, amino, mono lower alkylamino, or dilower alkylamino; or aralkyl.

The present invention is also a process for the preparation of a compound of formula II'

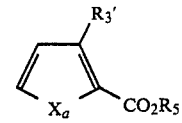

wherein $R_3'$ is OH, $X_a$ is NH or N-lower alkyl and $R_5$ is as defined above; which comprises contacting a compound of the formula $HX_aCH_2CO_2R_5'$ wherein $R_5'$ is lower alkyl with methyl α-haloacrylate wherein halo is bromo or chloro and then treating the resulting compound with a base to obtain a compound of the formula II'.

The compounds of formula I as defined above are active in the generally accepted assays showing the inhibition of the release of histamine from human basophils (HHB) and also the inhibition of the release of histamine from guinea pig chopped lung (FLAT), and, thus, are useful as antiallergic and antiinflammatory agents.

Therefore, the present invention is also a pharmaceutical composition for the treatment of allergies or inflammation comprising an antiallergic or antiinflammatory amount of a compound of the formula I and a pharmaceutically acceptable carrier therefor.

Additionally, the present invention is a method of treating allergies or inflammation in mammals, including man comprising administering to such mammals the compound of formula I as defined above.

The present invention is also processes for the preparation of the compound of formula I as defined above comprising contacting (1) an imidazole of formula II defined hereinafter which imidazole is treated with a coupling agent, and (2) an aminotetrazole.

A DETAILED DESCRIPTION OF THE INVENTION

In the present invention "lower alkyl" is alkyl of from one to six carbons, inclusive, and means methyl, ethyl, propyl, butyl, pentyl, or hexyl and isomers thereof.

"Lower alkoxy" means methoxy, ethoxy, propoxy, butoxy, pentoxy, or hexoxy and isomers thereof.

"Lower alkylthio" means methylmercapto, ethylmercapto, propylmercapto, butylmercapto, pentylmercapto, or hexylmercapto and isomers thereof.

"Aralkyl" is an aryl attached through a lower alkylenyl wherein the aryl means phenyl; unsubstituted or substituted with of from one to five, preferably from one to three substituents comprising one or more of each of halogen, trifluoromethyl, lower alkyl, hydroxy, lower alkoxy, nitro, amino, mono lower alkylamino, or dilower alkylamino. The lower alkylenyl means methylenyl, ethylenyl, propylenyl or butylenyl and isomers thereof.

"Halogen" is chloro, bromo, fluoro, or iodo.

Preferred compounds of the formula I are as follows:
3-Benzyloxy-5-methyl-N-1H-tetrazol-5-yl-2-thiophenecarboxamide;
4-Bromo-3-methoxy-5-methyl-N-1H-tetrazol-5-yl-2-thiophenecarboxamide;
4-Bromo-3-ethoxy-5-methyl-N-1H-tetrazol-5-yl-2-thiophenecarboxamide;

4-Bromo-3-(1-methylethoxy)-5-methyl-N-1H-tetrazol-5-yl-2-thiophenecarboxamide;

4-Bromo-3-benzyloxy-5-methyl-N-1H-tetrazol-5-yl-2-thiophenecarboxamide;

4,5-Dibromo-3-(1-methylethoxy)-N-1H-tetrazol-5-yl-2-thiophenecarboxamide;

4-Chloro-3-(1-methylethoxy)-N-1H-tetrazol-5-yl-2-thiophenecarboxamide;

4-Bromo-5-methoxy-3-(1-methylethoxy)-N-1H-tetrazol-5-yl-2-thiophenecarboxamide;

4,5-Dibromo-3-(1-methylethoxy)-1-methyl-N-1H-tetrazol-5-yl-1H-pyrrole-2-carboxamide;

3-(1-Methylethylthio)-5-trimethylsilyl-N-1H-tetrazol-5-yl-2-furancarboxamide;

3-(1-Methylethylthio)-N-1H-tetrazol-5-yl-2furancarboxamide; and

5-Bromo-3-(1-methylethylthio)-N-1H-tetrazol-5-yl-2-furancarboxamide.

Generally, the compounds of formula I as defined above are prepared in a novel process which comprises treating a compound of the formula (II)

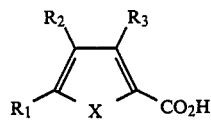

wherein $R_1$, $R_2$, $R_3$ and X are as defined above; with a coupling agent, such as 1,1-carbonyldiimidazole (CDI , Dicyclohexylcarbodiimide (DCC), or the like in a solvent, such as tetrahydrofuran, dimethyl formamide, acetonitrile, or the like, in an inert atmosphere at about reflux temperature for from one-half to three hours, preferably about one and a half hours. Then 5-aminotetrazole is added to the reflux mixture and heated under reflux conditions for an additional 1½ to 5 hours. The following Scheme I shows the process:

Scheme I

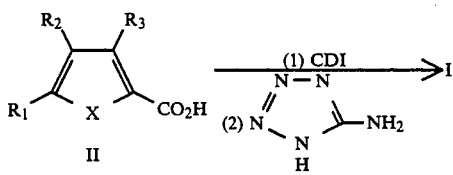

The compounds of the formula II wherein X is $S(O)_{0-2}$ or O are prepared by procedures either known or analogous to those known in the art.

However, the compounds of formula II wherein X is NH or $NR_4$ wherein $R_4$ is as defined above having $R_3$ as hydroxy or lower alkoxy and mercapto, lower alkylthio, lower alkylsulfinyl or lower alkoxysulfonyl are prepared by the novel process shown in the following Scheme II:

Scheme II

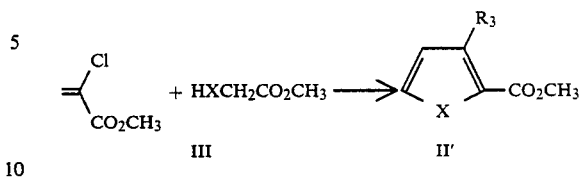

wherein $R_3$ is limited to hydroxy and X is limited to NH or $NR_4$.

The Scheme II is generally carried out by first combining methyl α-haloacrylate wherein halo is preferably chloro or bromo with or without a solvent. The solvent, that may be used includes, for example methanol, ethanol and the like. Initially, the reaction is accomplished at a temperature of from 0° to 35° C. preferably about 20° C. from about 5 minutes to 5 hours. The product of the initial combination may or may not be isolated and is subsequently added to a base in a solvent such as methanol or ethanol. The base may be sodium hydroxide, potassium hydroxide, or sodium, or potassium, alkoxide such as methoxide, ethoxide or t-butoxide. The basic mixture is again stirred at 0° to 35° C., preferably 20° C. for from about 5 minutes to 5 hours to give the product of formula II'. Optionally further, the compound of formula II' is treated by methods known or methods analogous to those known to obtain the compounds of formula II' wherein $R_3$ is as defined above other than hydroxy and wherein $R_4$ is as defined above other than hydrogen or methyl.

The compounds of formula I are useful both in the free acid form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as methanesulfonic acid, benzenesulfonic acid, p-toluenesulfonic acid, and the like, giving the hydrochloride, sulfamate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, carbonates, and bicarbonates of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di- or trihydroxyalkylamines such as mono-, di- and triethanolamine; amino acids such as arginine, and lysine; guanidine; N-methylglucosamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1), 1–19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The base salts of compounds of formula I described above are prepared by reacting the appropriate base with a stoichometric equivalent of the acid compounds of formula I to obtain pharmacologically acceptable base salts thereof.

The acid solution salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may also exist in hydrated or solvated forms.

The products of the reactions described herein are isolated by conventional means such as extraction, distillation, chromatography and the like.

The antiallergic and antiinflammatory ativity of the compounds having the formula I of the present invention is determined by an assay showing inhibition of the release of histamine from human basophils (HHB) and inhibition of the release of histamine from guinea pig chopped lung (FLAT). A description of the protocol for each of the HHB and FLAT assays is found hereinafter.

Thus, pharmaceutical compositions are prepared from the compounds of formula I and salts thereof described as the present invention in unit dosage form comprising the compound either alone or in admixture with a pharmaceutically acceptable carrier appropriately selected from those known.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area, (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound I is employed in treatment. The ordinarily skilled physician or veterinarian will readily determine and prescribe the effective amount of the antiallergic or antiinflammatory agent to prevent or arrest the progress of the condition. The dosage regimen is selected in accordance with a variety of factors including the type, age, weight, sex, and medical condition of the mammal, the severity of symptoms of the disease being treated, the route of administration and particular compound of formula I employed. An ordinarily skilled physician or veterinarian will readily determine and prescribe the effective amount of the compound I to prevent or arrest the progress of the condition. In so proceeding, the physician or veterinarian could employ relatively low dosages at first, subsequently increasing the dose until a maximum response is obtained. For convenience, the total daily dosage may be divided and administered in portions during the day if desired. In so proceeding, the physician or veterinarian could employ relatively low dosages at first, subsequently increasing the dose until a maximum response is obtained.

Initial dosages of the compounds of the invention having formula I are ordinarily in the area of 10 mg up to 2 g per day orally, preferably 10 mg to 500 mg per dose orally, given from one to four times daily or as needed. When other forms of administration are employed equivalent doses are administered.

It is understood that the compositions and methods of treatment of the present invention as described above also include the free acid, the pharmacologically acceptable base salts and acid addition salts of the compounds of formula I.

The following Examples further illustrate the invention, but are not meant to be limiting thereto.

EXAMPLE 1

Methyl 3-hydroxy-5-phenyl-2-thiophenecarboxylate.

A mixture of ethyl benzoylacetate (192 g, 1.0 mole) and methyl thioglycolate (212 g, 2.0 moles) is stirred under argon and cooled to $-10°$ C., then saturated with dry gaseous HCl. After 1 hour the temperature is allowed to rise to ambient. After a total of 5 hours the mixture is stirred into ice water (3 L)) and extracted three times with ether. The combined extracts are washed with 5% aqueous $Na_2CO_3$ twice, then with water once, and dried over sodium sulfate. The solvent is removed under reduced pressure and the residue is stirred overnight under vacuum, leaving 298 g of clear yellow oil. This is added dropwise to a stirred solution of sodium (62.6 g, 2.7 moles) in methanol (1.4 L) under argon. After 70 minutes at room temperature the mixture is poured into ice water (1 L), stirred well and acidified with concentrated hydrochloric acid. The precipitate is filtered off, rinsed with water and dried to afford the product (132 g); mp 92°–95° C.

EXAMPLE 2

Methyl 3-hydroxy-4,5-dimethyl-2-thiophenecarboxylate.

Prepared by the method descrihed in Example 1 from ethyl α-methyl acetoacetate (29 g, 0.20 moles), methyl thioglycolate (45 g, 0.40 moles) and sodium (10.2 g, 0.44 moles). Recrystallization from methanol gave the product (15.2 g); mp 52°–54° C.

EXAMPLE 3

Methyl 3-hydroxy-5-methyl-2-thiophenecarboxylate.

Prepared by the method described in Example 1 from ethyl acetoacetate (130 g, 1.0 mole), methyl thioglycolate (212 g, 2.0 moles) and sodium (53 g, 2.3 moles). The crude product is shaken with two portions of dichloromethane, filtered, and the filtrate stripped of solvent under reduced pressure to afford the product (90.1 g); mp 50°–53° C.

EXAMPLE 4

Methyl 4-bromo-3-hydroxy-5-methyl-2-thiophenecarboxylate.

Bromine (4.6 g, 29 mmoles) is added dropwise at room temperature to a stirred solution of methyl 3-hydroxy-5-methyl-2-thiophenecarboxylate (5.0 g, 29 mmoles) in acetic acid (25 mL). After 16 hours the mixture is stirred into ice water (200 mL), and the precipitate is filtered off, rinsed with water, with aqueous sodium thiosulfate, again with water and dried. Recrystallization from methyl t-butyl ether gave the pure product (4.1 g); mp 96°–97° C.

EXAMPLE 5

Methyl 3-hydroxy-4-bromo-5-phenyl-2-thiophenecarboxylate.

Prepared by the method described in Example 4 from methyl 3-hydroxy-5-phenyl-2-thiophenecarboxylate (5.0 g, 21 mmoles) and bromine (3.4 g, 21 mmoles). Recrystallization from methanol gave the product (4.0 g); mp 85°–87° C.

EXAMPLE 6

Methyl 3-hydroxy-2thiophenecarboxylate.

A solution of methyl thioglycolate (19.2 g, 181 mmoles) in methanol (100 mL) is added to a solution of sodium (8.0 g, 348 mmoles) in methanol (100 mL) with stirring, and cooling with an ice bath. A solution of methyl α-chloroacrylate (22.1 g, 183 mmoles) in methanol (25 mL) is then added at such a rate that the temperature does not exceed 30° C. After 1 hour at ambient temperature, the methanol is removed under reduced pressure. The residue is dissolved in water, acidified with HCl and steam distilled until the distillate is clear. The distillate is cooled and shaken, and the resulting precipitate filtered off, rinsed with water and dried to afford the product (21.3 g); mp 43°–45° C.

EXAMPLE 7

Methyl 3-hydroxy-4-bromo-2-hiophenecarboxylate.

Prepared by the method described in Example 4 from methyl 3-hydroxy-2-thiophenecarboxylate (12.0 g, 76 mmoles) and bromine (12.1 g, 76 mmoles). Recrystallization from methanol gave the product (9.4 g); mp 79°–81° C.

EXAMPLE 8

Methyl 3-hydroxy-4,5-dibromo-2-thiophenecarboxylate.

Methyl 3-hydroxy-2-thiophenecarboxylate (12.0 g, 76 mmoles) is dissolved in acetic acid (35 mL) and stirred at room temperature. Bromine (27.5 g, 172 mmoles) is added in one portion. After 20 hours the suspended solid is filtered off, rinsed with cold isopropanol and dried to afford the pure product (10.9 g); mp 130°–131° C.

EXAMPLE 9

Methyl 3-hydroxy-4-(1-methylethyl)-5-methyl-2-thiophenecarboxylate.

Prepared by the method described in Example 1 from ethyl α-isopropylacetoacetate (prepared by the procedure of Manuel and Hagen, Org. Syn., 7, 248 (1951)) (12 g, 70 mmoles), methyl thioglycolate (15.7 g, 140 mmoles) and sodium (3.2 g, 139 mmoles). The product is extracted with CH$_2$Cl$_2$ twice. The combined extracts are washed with aqueous NaCl twice, dried over MgSO$_4$ and stripped of solvent under reduced pressure. Distillation of the residue gave the product (3.3 g); bp 68°–71° C. (0.3 mmHg).

EXAMPLE 10

Methyl 3-hydroxy-4-chloro-5-methyl-2-thiophenecarboxylate.

Prepared by the method described in Example 1 from ethyl α-chloroacetoacetate (59 g, 0.35 moles), methyl thioglycolate (102 g, 0.70 moles) and sodium (19.7 g, 0.86 moles). The product is obtained from the crystalline precipitate by fractional recrystallization from isopropanol to give 2.8 g; mp 105°–107° C.

EXAMPLE 11

Methyl 3-hydroxy-4,5-dichloro-2-thiophenecarboxylate.

A mixture of methyl 3-hydroxy-2-thiophenecarboxylate (10.0 g, 63 mmoles) and N-chlorosuccinimide (22.0 g, 165 mmoles) is stirred in acetic acid (50 mL) under argon and heated to 85° C. After 4 hours the mixture is stirred into ice water (175 mL) and extracted three times with ether. The combined extracts are washed with aqueous NaCl twice, then aqueous KHCO$_3$ until the washings remain basic. The organic solution is dried over MgSO$_4$ and the solvent is removed under reduced pressure. The residue is dissolved in acetic acid (35 mL) and stirred at room temperature while HCl gas is bubbled in for 15 minutes. The mixture is allowed to stand for 48 hours, and is then concentrated under reduced pressure. The precipitate is filtered off, rinsed with cold isopropanol and dried to afford the product (6.4 g); mp 109°–110° C.

EXAMPLE 12

Methyl 3-hydroxy-5-methylethyl-2-thiophenecarboxylate.

Prepared by the method described in Example 1 from ethyl isobutyrylacetate (47 g, 0.28 moles), methyl thioglycolate (59.9 g, 0.56 moles) and sodium (13.7 g, 0.60 moles). The product precipitates as the sodium salt prior to acidification of the workup mixture, and is filtered off, rinsed with ethanol and dried. The salt is stirred in water, acidified with concentrated HCl and the mixture extracted twice with aqueous NaCl and dried over MgSO$_4$. Removal of the solvent under reduced pressure afforded the product as a clear yellow oil, sufficiently pure for further use.

EXAMPLE 13

Methyl 3-hydroxy-4-bromo-5-methylethyl-2-thiophenecarboxylate.

Prepared by the method described in Example 4 from methyl 3-hydroxy-5-methylethyl-2-thiophenecarboxylate (3.0 g, 15 mmoles) and bromine (2.4 g, 15 mmoles). Recrystallization from isopropanol gave the product (1.9 g); mp 57°–59° C.

EXAMPLE 14

Methyl 3-hydroxy-4-bromo-5-methoxy-2-thiophenecarboxylate.

Sulfuryl chloride (3.1 mL, 37 mmoles) is added dropwise at room temperature to a stirred solution of methyl 3-hydroxy-4-bromo-2-thiophenecarboxylate (8.2 g, 35 mmoles) in chloroform (40 mL) under argon. After 24 hours the mixture is evaporated under reduced pressure and the residue is stirred in methanol (25 mL). After another 24 hours the precipitate is filtered off, rinsed with methanol and dried to give the product (4.2 g); mp 107°–109° C.

EXAMPLE 15

Methyl 3,4-dihydroxy-5-methyl-2-thiophenecarboxylate.

A mixture of dimethyl α-methyl-thiodiglycolate (Solladie-Cavallo, *Bull. Soc. Chim. Fr.*, 437 (1968)) (10.2 g, 53 mmoles) and dimethyl oxalate (9.4 g, 79 mmoles) in methanol (25 mL) is added slowly to a solution of sodium (3.8 g, 165 mmoles) in methanol (35 mL) under argon and maintained at 10°–15° C. with an ice bath. After the addition, the mixture is slowly heated to reflux for 1 hour, then cooled and concentrated under reduced pressure. The precipitate is filtered off, rinsed with ether, air dried, dissolved in water and acidified with 4N hydrochloric acid. The precipitate is filtered off, rinsed with water and dried to afford the product (6.8 g); mp 116°–117° C.

EXAMPLE 16

Methyl 3,4-dihydroxy-5-phenyl-2-thiophenecarboxylate.

Prepared by the method described in Example 15 from dimethyl α-phenyl-thiodiglycolate (9.0 g, 35 mmoles), dimethyl oxalate (6.1 g, 52 mmoles) and sodium (2.5 g, 109 mmoles). The product is obtained as a beige powder (3.8 g); mp 143°–144° C.

Various thiophenes used as starting materials are prepared by methods known or methods analogous to those known. For example, the thiophenes of Examples 7, 8 and 11 are prepared by a method such as is described by Corral and Lissavetzky, *Syn.*, 847–50 (1984); the thiophenes of Example 6 are prepared by a method such as is described by Huddleston and Barker, *Syn. Com.*, 731–34 (1979); the thiophenes of Example 14 are prepared by a method such as is described by Corral and Lissavetzky, *J. Chem. Soc. Perk. I.*, 2711–14 (1984); the thiophenes of Examples 1 and 3 are prepared by a method such as is described by Brelivet, et al., *Bull. Soc. Chim. Fr.*, 4, 1344–51 (1971).

The thiophenes of use in the corresponding Examples 1–16 above are prepared having the melting points as shown in the following Table 1.

TABLE 1

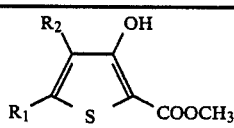

| Example No. | $R_1$ | $R_2$ | mp °C. |
|---|---|---|---|
| 1 | Ph | H | 92–95 |
| 2 | Me | Me | 52–54 |
| 3 | Me | H | 50–53 |
| 4 | Me | Br | 96–97 |
| 5 | Ph | Br | 85–87 |
| 6 | H | H | 43–45 |
| 7 | H | Br | 96–97 |
| 8 | Br | Br | 130–131 |
| 9 | Me | iPr | 68–71 at 0.3 mm pressure |
| 10 | Me | Cl | 105–107 |
| 11 | Cl | Cl | 109–110 |
| 12 | iPr | H | — |
| 13 | iPr | Br | 57–59 |
| 14 | MeO | Br | 107–109 |

TABLE 1-continued

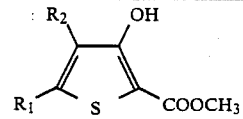

| Example No. | $R_1$ | $R_2$ | mp °C. |
|---|---|---|---|
| 15 | Me | OH | 116–117 |
| 16 | Ph | OH | 146–147 |

In the table Ph is phenyl, Me is methyl, iPr is isopropyl, and MeO is methoxy. Of course H, Br, Cl, and OH are as generally accepted in the art.

EXAMPLE 17

Dimethyl α-methyl-thiodiglycolate.

A mixture of methyl 2-bromopropionate (8.9 g, 53 mmoles) and diisopropylethylamine (6.9 g, 53 mmoles) is cooled in an ice bath while methyl thioglycolate (5.6 g, 53 mmoles) is added dropwise. The ice bath is removed and the mixture stirred at room temperature for 12 hours, then diluted with water (150 mL) and extracted twice with ether. The combined extracts are washed with aqueous NaCl and dried over MgSO$_4$. The solvent is removed under reduced pressure and the residue is distilled to afford the product (9.0 g) as a clear, colorless oil; bp 72°–74° C.$^{0.8}$ mm.

EXAMPLE 18

Dimethyl α-phenyl-thiodiglycolate.

Prepared by the method described in Example 17 from methyl α-bromophenylacetate (11.6 g, 48 mmoles), methyl thioglycolate (5.1 g, 48 mmoles), and triethyl amine (4.9 g, 48 mmoles). Removal of the solvent under reduced pressure leaves the product as a clear oil (9.5 g) sufficiently pure for further use.

EXAMPLE 19

Methyl 3-methoxy-4,5-dimethyl-2-thiophenecarboxylate.

Methyl 3-hydroxy-4,5-dimethoxy-2-thiophenecarboxylate (5.0 g, 27 mmoles) is dissolved in acetone (50 mL) under nitrogen. Potassium carbonate (4.5 g, 32 mmoles) is added followed by dimethyl sulfate (4.2 g, 32 mmoles) and the mixture is stirred and heated under reflux. After 18 hours the mixture is stripped of solvent under reduced pressure, and the residue is partitioned between water (100 mL) and dichloromethane (100 mL). After separation the aqueous layer is extracted with dichloromethane (75 mL). The combined organic extracts are washed twice with brine, dried over MgSO$_4$, and stripped of solvent under reduced pressure. Recrystallization of the residue from pentane gave the product (3.4 g); mp 37°–39° C.

EXAMPLE 20

Methyl 3-(1-methylethoxy)-5-phenyl-2-thiophenecarboxylate.

Methyl 3-hydroxy-5-phenyl-2-thiophenecarboxylate (20.0 g, 85 mmoles) is dissolved in dimethylsulfoxide (80 mL) under argon and cooled in an ice bath. Potassium t-butoxide (10.1 g, 90 mmoles) is added, followed after 25 minutes by 2-bromopropane (22.1 g, 180 mmoles), and the ice bath is removed. After 24 hours the mixture is heated to 80° C. for 1 hour, then poured into ice water (500 mL), stirred, and acidified with concentrated HCl.

The mixture is extracted with dichloromethane (3×200 mL) and the combined extracts are washed with brine, dried over MgSO$_4$ and stripped of solvent under reduced pressure to leave the product as a syrupy residue (22.1 g) sufficiently pure for further use.

EXAMPLE 21

Methyl 3-(1-methylethoxy)-5-methyl-2-thiophenecarboxylate.

Methyl 3-hydroxy-5-methyl-2-thiophenecarboxylate (20.0 g, 116 mmoles) is dissolved in acetonitrile (450 mL) under argon. Triisopropylisourea (86.6 g, 465 mmoles) is added and the mixture stirred and heated under reflux. After 24 hours the mixture is cooled and the precipitate filtered off, rinsed with cold MeCN and discarded. The filtrate is stripped of solvent by rotary evaporator, then the excess triisopropylisourea is removed by distillation under reduced pressure. The remaining residue is dissolved in a small amount of ethyl acetate, cooled, filtered, and passed through a short column of silica gel. Evaporation of the effluent under reduced pressure leaves the product as an oil (18.8 g) sufficiently pure for further use.

The compounds in Table 2 are prepared by the methods as indicated in Examples 19, 20 and 21.

TABLE 2

$R_2$—⟨thiophene with $R_1$, S, COOCH$_3$⟩—$R_3$

| Example No. | R$_1$ | R$_2$ | R$_3$ | Prepared by Method of Example No. | mp °C. |
|---|---|---|---|---|---|
| 22 | Ph | H | MeO | 19 | 64–65 |
| 23 | Ph | H | EtO | 19 (using diethylsulfate) | 81–82 |
| 24 | Ph | H | BnO | 19 (using benzylbromide) | 79–81 |
| 25 | Ph | Br | iPrO | 19 | — |
| 26 | Me | H | BnO | 19 (using benzylbromide) | — |
| 27 | Me | Me | EtO | 19 (using diethylsulfate) | — |
| 28 | Me | Me | iPrO | 20 | — |
| 29 | Me | Br | MeO | 19 | 77–79 |
| 30 | Me | Br | EtO | 19 (using diethylsulfate) | — |
| 31 | Me | Br | iPrO | 21 | — |
| 32 | Me | Br | BnO | 19 (using benzylbromide) | 70–71 |
| 33 | H | Br | iPrO | 21 | — |
| 34 | Br | Br | iPrO | 21 | 57–59 |
| 35 | Me | OMe | MeO | 19 | — |
| 36 | Me | OiPr | iPrO | 21 | — |
| 37 | Me | iPr | iPrO | 21 | — |
| 38 | Me | Cl | iPrO | 21 | — |
| 39 | iPr | H | iPrO | 20 | — |
| 40 | iPr | Br | iPrO | 21 | — |
| 41 | Cl | Cl | iPrO | 21 | — |
| 42 | MeO | Br | iPrO | 21 | — |
| 43 | Ph | OiPr | iPrO | 21 | — |

Ph, Me, iPr, and MeO are as defined above for Table 1. Additionally, Bn is benzyl and Et is ethyl herein Table 2. EtO is ethoxy, BnO is benzyloxy, and iPrO is isopropoxy. The remainder of the R$_1$ or R$_2$ abbreviations are as understood in the art.

EXAMPLE 44

3-Ethoxy-5-phenyl-2-thiophenecarboxylic acid.

A solution of methyl 3-ethoxy-5-phenyl-2-thiophenecarboxylate (12.0 g, 46 mmoles) in tetrahydrofuran (150 mL) is added to a solution of potassium hydroxide (14.6 g, 229 mmoles) in water (150 mL). The mixture is stirred and heated under reflux for 24 hours, then the tetrahydrofuran is removed using a rotary evaporator. The aqueous suspension is cooled in an ice bath and acidified with concentrated HCl. The precipitate is collected by filtration, rinsed well with water and dried to afford the pure product (10.6 g); mp 174°–175° C.

EXAMPLE 45

4-Bromo-3-(1-methylethoxy)-5-phenyl-2-thiophenecarboxylic acid.

Methyl 4-bromo-3-(1-methylethoxy)-5-phenyl-2-thiophenecarboxylate (4.8 g, 14 mmoles) is stirred in methanol (5 mL), 1N NaOH (27 mL) is added, and the mixture is stirred and heated under reflux. After 3 hours the mixture is stirred into water (300 mL) and acidified with concentrated HCl. The precipitate is filtered off, rinsed with water and dried to afford the product (4.7 g); mp 159°–160° C.

Again the Examples in the following Table 3 are of compounds as prepared by a method analogous to the indicated Examples 44 or 51.

TABLE 3

$R_2$—⟨thiophene with $R_1$, S, COOH⟩—$R_3$

| Example No. | R$_1$ | R$_2$ | R$_3$ | Prepared by Method of Example No. | mp °C. |
|---|---|---|---|---|---|
| 46 | Ph | H | MeO | 44 | 154–5 |
| 47 | Ph | H | iPrO | 44 | 143–5 |
| 48 | Ph | H | BnO | 44 | 171–4 |
| 49 | Me | H | iPrO | 45 | 110–11 |
| 50 | Me | H | BnO | 45 | 152–3 |
| 51 | Me | Me | MeO | 44 | 139–40 |
| 52 | Me | Me | EtO | 44 | 125–6 |
| 53 | Me | Me | iPrO | 44 | 133–4 |
| 54 | Me | Br | MeO | 51 | 172–3 |
| 55 | Me | Br | EtO | 51 | 157–8 |
| 56 | Me | Br | iPrO | 51 | 129–30 |
| 57 | Me | Br | BnO | 51 | 172–3 |
| 58 | H | Br | iPrO | 51 | 127–8 |
| 59 | Br | Br | iPrO | 51 | 138–42 |
| 60 | H | MeO | MeO | * | 131–2 |
| 61 | Me | MeO | MeO | 51 | 132–3 |
| 62 | Me | OiPr | iPrO | 51 | 82–4 |
| 63 | Me | iPr | iPrO | 51 | 163–4 |
| 64 | Me | Cl | iPrO | 51 | 132–4 |
| 65 | iPr | H | iPrO | 51 | 87–89 |
| 66 | iPr | Br | iPrO | 51 | 131–2 |
| 67 | Cl | Cl | iPrO | 51 | 133–4 |
| 68 | MeO | Br | iPrO | 51 | 115–16 |
| 69 | Ph | OiPr | iPrO | 51 | 159–60d |

*Fager, J. Am. Chem. Soc., 67, 2217 (1945).

Each of the noted substituents R$_1$, R$_2$ and R$_3$ in Table 3 are as defined in Tables 1 and 2 above.

EXAMPLE 70

3-Methoxy-4,5-dimethy-N-1H-tetrazol-5-yl-2-thiophenecarboxamide.

1,1'-Carbonyldiimidazole (4.1 g, 25 mmoles) is added to a solution of 3-methoxy-4,5-dimethyl-2-thiophenecarboxylic acid (4.5 g, 24 mmoles) in tetrahydrofuran (80 mL) under argon. The mixture is stirred and heated under reflux for 1.5 hours. 5-Aminotetrazole (2.0 g, 24 mmoles) is added and heating under reflux is continued for an additional 2.5 hours. The mixture is cooled, and the precipitate is filtered off, rinsed with tetrahydrofuran, dried, and stirred in 2N HCl. After 10 minutes the suspended solid is collected by filtration, rinsed with water and dried to afford the product (4.4 g); mp 229° C. (dec).

EXAMPLE 71

4-Bromo-3-(1-methylethoxy)-N-1H-tetrazol-5-yl-2-thiophenecarboxamide.

1,1'-Carbonyldiimidazole (2.2 g, 14 mmoles) is added to a solution of 4-bromo-3-(1-methylethoxy)-2-thiophenecarboxylic acid (3.5 g, 13 mmoles) in tetrahydrofuran (50 mL) under argon. The mixture is stirred and heated under reflux for 1.5 hours. 5-Aminotetrazole (1.1 g, 13 mmoles) is added, and heating under reflux continued for 2.5 additional hours. The mixture is then stirred into ice water (200 mL) and acidified with concentrated HCl. After 1 hour the precipitate is filtered off, rinsed with water and dried to afford the product (4.1 g); mp 193°–194° C.

TABLE 4

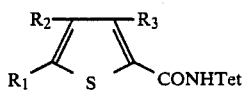

| Example No. | $R_1$ | $R_2$ | $R_3$ | Prepared by Method of Example No. | mp °C. |
| --- | --- | --- | --- | --- | --- |
| 72 | Ph | H | MeO | 70 | 237–8 |
| 73 | Ph | H | EtO | 70 | 264d |
| 74 | Ph | H | iPrO | 70 | 256d |
| 75 | Ph | H | BnO | 70 | 249d |
| 76 | Ph | Br | iPrO | 71 | 226–7 |
| 77 | Me | H | iPrO | 70 | 235d |
| 78 | Me | H | BnO | 70 | 238d |
| 79 | Me | Me | EtO | 70 | 239–40d |
| 80 | Me | Me | iPrO | 70 | 246d |
| 81 | Me | Br | MeO | 71 | 208–9d |
| 82 | Me | Br | EtO | 71 | 211–13d |
| 83 | Me | Br | iPrO | 70 | 117d |
| 84 | Me | Br | BnO | 70 | 199–200d |
| 85 | Br | Br | iPrO | 71 | 230d |
| 86 | H | MeO | MeO | 71 | 216d |
| 87 | Me | MeO | MeO | 71 | 222d |
| 88 | Me | OiPr | iPrO | 71 | 193–5 |
| 89 | Me | iPr | iPrO | 71 | 136–7 |
| 90 | Me | Cl | iPrO | 71 | 214–15 |
| 91 | iPr | H | iPrO | 71 | 190–91 |
| 92 | iPr | Br | iPrO | 71 | 218–19 |
| 93 | Cl | Cl | iPrO | 71 | 228d |
| 94 | MeO | Br | iPrO | 71 | 211–12 |
| 95 | Ph | OiPr | iPrO | 71 | 200–08 |

Each of the noted substitutents $R_1$, $R_2$, and $R_3$ in Table 4 are as defined in Tables 1 and 2 above.

EXAMPLE 96

2-Thiophenecarboxamide,3-methoxy -N-1H-tetrazol-5-yl-, comp. with 1Himidazole (1:1).

A mixture of 3-methoxy-2-thiophenecarboxylic acid (Salo Granowitz, *Arkiv Fur Kemi.* 12, 239–246 (1958)) (6.0 g, 0.038 mole) and 1,1'-carbonyldiimidazole (6.14 g, 0.038 mole) in tetrahydrofuran (250 mL) is stirred at room temperature for 80 minutes under nitrogen. To this solution 5-amino-tetrazole (3.23 g, 0.038 mole) is added and the mixture is stirred at room temperature for 19 hours. Filtration of the resulting solid (6.2 g, mp 176°–8° C.) and recrystallization from methanol gives 4.5 g of analytically pure product; mp 176°–8° C.

EXAMPLE 97

2-Thiophenecarboxamide,3-(4-methylphenoxy)-N-1H-tetrazol-5-yl.

A mixture of 3-(p-tolyloxy)thiophene-2-carboxylic acid (Jeffrey W. H. Watthey and Mahesh Desai, *J. Org. Chem.*, 47(9), 1755–9 (1982)) (7.03 g, 0.03 mole) and 1,1'-carbonyldiimidazole (4.86 g, 0.03 mole) in tetrahydrofuran (200 mL) is stirred at room temperature for 135 minutes under nitrogen. To this solution 5-aminotetrazole (2.55 g, 0.03 mole) is added. The reaction mixture is stirred at room temperature for 21 hours, then heated under reflux for 75 minutes. The solvent is removed <45° C. in vacuo to give a residue. Recrystallization from methanol-ethyl acetate, then from methanol gives 3.58 g of analytically pure product; mp 258°–260° C.

EXAMPLE 98

2-Thiophenecarboxamide,3-(4-methoxyphenylthio)-N-1H-tetrazol-5-yl.

Stage A. 3-(4-Methoxyphenylthio)thiophene.

A mixture of 3-bromothiophene (50 g, 0.31 mole), p-methoxybenzenethiol (45.2 g, 0.31 mole), cuprous oxide (22.7 g, 0.15 mole), potassium hydroxide (20.3 g, 0.31 mole) and dimethylformamide (300 mL) is refluxed for 66 hours under nitrogen. The reaction mixture is cooled and poured into a 1:1 mixture of 6N hydrochloric acid and ice. The mixture is extracted with toluene. The combined toluene extracts are washed with aqueous sodium hydroxide solution and water. After evaporation of the solvent under vacuum the crude oil (33 g) is distilled to give 22 g of colorless oil; bp 140° C. (0.1 mmHg).

Stage B. 3-(4-Methoxyphenylthio)thiophene-2-carboxylic acid.

A solution of phenyllithium in cyclohexane-ether (39.5 mL, 2.7 m) is added dropwise to a stirred solution of 3-(4-methoxyphenylthio)thiophene (21.44 g, 0.096 mole) in dry ether (150 mL) at 0° C. After stirring at 0° C. for 5 hours the solution is poured into a dry ice/ether mixture at −78° C., stirred at this temperature for 1 hour. The mixture is warmed to room temperature and water is added (300 mL). The layers are separated, and the aqueous phase is extracted with ether. The aqueous phase is carefully acidified with aqueous hydrochloric acid, while the temperature is maintained below 15° C. and extracted with ether. The ether solution is dried over sodium sulfate and the solvent is removed under reduced pressure to give 14.5 g of a solid; mp 220°–2° C. (dec). Recrystallization from acetonitril gives 8.5 g of a product; mp 220°–2° C. (dec).

Stage C. 2-Thiophenecarboxamide,3-(4-methoxyphenylthio)-N-1H-tetrazol-5-yl.

A mixture of 3-(4-methoxyphenylthio)thiophene-2-carboxylic acid (7.9 g, 0.034 mole) and 1,1'-carboxyldiimidazole (6.55 g, 0.04 mole) in acetonitrile (250 mL) is refluxed with stirring under nitrogen for 1¾ hours. A solution of 5-aminotetrazole (3.44 g, 0.04 mole) and triethylamine (4.09 g, 0.04 mole) in acetonitrile (150 mL) is added dropwise. The mixture is heated at reflux for 17.5 hours, then most of the acetonitrile is removed under water aspirator pressure at 40° C. The residue is treated with cold water (800 mL), then acidified with acetic acid (13 mL). The resulting solid is separated by filtration, washed with water, then with ether and dried to give 11.1 g of a solid. Recrystallization from dimethylformamide-methanol gives 6.5 g (58%) of analytically pure product; mp 245°–7° C. (dec).

EXAMPLE 99

Ethyl 3-hydroxy-1-phenyl-1H-pyrrole-2-carboxylate.

Ethyl 3-hydroxy-1-phenyl-1H-pyrrole-2-carboxylate was prepared using the procedure of Momose, et al, *Chem. Pharm. Bull.*, 26, 2224 (1978).

EXAMPLE 100

Ethyl 3-hydroxy-1-(phenylmethyl)-1H-pyrrole-2-carboxylate.

Ethyl 3-hydroxy-1-(phenylmethyl)-1H-pyrrole-2carboxylate was prepared using the method of Momose, et al, *Chem. Pharm. Bull.*, 26, 2224 (1978).

EXAMPLE 101

Methyl 3-hydroxy-1-methyl-1H-pyrrole-2-carboxylate.

Methyl sarcosinate (14.5 g, 0.14 moles) is added dropwise to methyl α-chloroacrylate (16.9 g, 0.14 moles), stirred and cooled in an ice bath. After 15 minutes the mixture is dissolved in methanol (30 mL) and added dropwise to a solution of sodium (9.7 g, 0.42 moles) in methanol (125 mL) under argon. After 18 hours at room temperature, the mixture is striped of methanol under reduced pressure. The residue is taken up in water (300 mL), acidified with $H_3PO_4$, and extracted with ethyl acetate (5×100 mL). The combined extracts are dried over $MgSO_4$, concentrated under reduced pressure and filtered through a short column of silica gel. The filtrate is stripped of solvent under reduced pressure, leaving the product (16.5 g) as an oil sufficiently pure for further use. An analytically pure sample was obtained by vacuum distillation; bp 61°–64° C. (0.5 mm) followed by recrystallization of the distillate from n-pentane to afford the product as shiny white crystals; mp 44°–46° C.

EXAMPLE 102

Methyl 3-hydroxy-1H-pyrrole-2-carboxylate.

Prepared by the method described in Example 101 from methyl glycinate (22 g, 0.25 moles), methyl α-chloroacrylate (29.8 g, 0.25 moles), and sodium (17 g, 0.74 moles). Following filtration through silica gel and evaporation of the filtrate, the product is obtained pure and crystalline (18.6 g ; mp 100°–102° C.

EXAMPLE 103

Ethyl 4,5-dibromo-3-hydroxy-1-phenyl-1H-pyrrole-2-carboxylate.

Ethyl 3-hydroxy-1-phenyl-1H-pyrrole-2-carboxylate (5.0 g, 0.022 moles) is dissolved in acetic acid (20 mL) and stirred at ambient temperature while bromine (2.4 mL, 0.047 moles) is added dropwise. After 1 hour the suspended solid is filtered off, rinsed with cold ethanol and dried, affording the pure product (7.8 g); mp 144°–145° C.

EXAMPLE 104

Ethyl 4,5-dibromo-3-hydroxy-1-(phenylmethyl -1H-pyrrole-2-carboxylate.

Prepared using the procedure described in Example 103 from ethyl 3-hydroxy-1-(phenylmethyl)-1H-pyrrole-2-carboxylate (3.1 g, 0.013 moles) and bromine (1.3 mL, 0.026 moles). Recrystallization from ethanol gave the pure product (3.9 g); mp 107°–108° C.

EXAMPLE 105

Methyl 4,5-dibromo-3-hydroxy-1-methyl-1H-pyrrole-2-carboxylate.

Methyl 3-hydroxy-1-methyl-1H-pyrrole-2-carboxylate (5.0 g, 0.032 moles) is dissolved in acetic acid (50 mL) and stirred at room temperature while bromine (3.3 mL, 0.065 moles) is added dropwise. After 1 hour the mixture is stirred into water (250 mL) and the precipitate is collected by filtration, rinsed several times with water and dried to afford the pure product (6.9 g); mp 128°–130° C.

EXAMPLE 106

Methyl 3-(1-methylethoxy)-1H-pyrrole-2-carboxylate.

Methyl 3-hydroxy-1H-pyrrole-2-carboxylate (2.0 g, 0.014 moles) is dissolved in DMF (15 mL) under nitrogen. Potassium carbonate (2.8 g, 0.020 moles) is added followed by 2-bromopropane (5 mL, 0.05 moles) and the mixture is stirred at room temperature for 18 hours, then at 50° C. for 3 hours, then stirred into ice water (400 mL). The mixture is extracted with $CH_2Cl_2$ (3x) and the combined extracts are washed with brine (2x) and dried over $MgSO_4$. Removal of the solvent under reduced pressure leaves the crude product as a crystalline residue. Recrystallization from ether gave the pure product (1.6 g); mp 77°–79° C.

EXAMPLE 107

Ethyl 4,5-dibromo-3-(1-methylethoxy)-1-phenyl-1H-pyrrole-2-carboxylate.

Ethyl 4,5-dibromo-3-hydroxy-1-phenyl-1H-pyrrole-2-carboxylate (4.0 g, 0.010 moles) is dissolved in DMSO (20 mL) under argon. Potassium tert-butoxide (1.2 g, 0.011 moles) is added, followed after 15 minutes by 2-bromopropane (2.6 mL, 0.021 moles), and the mixture is stirred at room temperature. After 24 hours the mixture is stirred into ice water (300 mL) and extracted with $CH_2Cl_2$ (3×125 mL). The combined extracts are washed with saturated brine (2×100 mL) and dried over $MgSO_4$. Removal of the solvent under reduced pressure left the product (4.1 g) as an oil, sufficiently pure for further use.

EXAMPLE 108

Ethyl 4,5-dibromo-3-(1-methylethoxy)-1-(phenylmethyl)-1H-pyrrole-2-carboxylate.

Prepared using the method described in Example 107 from ethyl 4,5-dibromo-3-hydroxy-1-(phenylmethyl)-1H-pyrrole-2-carboxylate (3.2 g, 0.008 moles), potassium tert-butoxide (1.0 g, 0.009 moles) and 2-bromopropane (2.0 g, 0.016 moles). The product crystallized upon aqueous workup and was filtered off, rinsed with water and dried to afford the pure product (3.0 g); mp 46°–48° C.

EXAMPLE 109

Methyl 4,5-dibromo-3-(1-methylethoxy)-1-methyl-1H-pyrrole-2-carboxylate.

Methyl 4,5-dibromo-3-hydroxy-1-methyl-1H-pyrrole- 2-carboxylate (9.6 g, 0.03 moles) and potassium carbonate (5.0 g, 0.036 moles) are stirred in a mixture of acetone (100 mL) and DMF (15 mL) and heated to reflux under argon. After 22 hours the solvent is removed under reduced pressure and the residue is partitioned between $CH_2Cl_2$ (500 mL) and water (400 mL). The layers are separated and the aqueous phase is extracted with $CH_2Cl_2$ (300 mL). The combined organic extracts are washed with saturated brine (2×300 mL) and dried over $MgSO_4$. Removal of the solvent under reduced pressure afforded the crystalline product (10.6 g); mp 42°–45° C.

EXAMPLE 110

Methyl 4,5-dibromo-3-(1-methylethoxy)-1H-pyrrole-2-carboxylate.

Prepared using the method described in Example 103 from methyl 3-(1-methylethoxy)-1H-pyrrole-2-carboxylate (1.5 g, 0.008 moles) and bromine (0.84 mL, 0.016 moles). The product was obtained as a crystalline powder (2.2 g); mp 124°–125° C.

EXAMPLE 111

4,5-Dibromo-3-(1-methylethoxy)-1-phenyl-1H-pyrrole-2-carboxylic acid.

Ethyl 4,5-dibromo-3-(1-methylethoxy)-1-phenyl-1H-pyrrole-2-carboxylate (3.0 g, 0.007 moles) is dissolved in methanol (40 mL), 2N NaOH (20 mL) is added and the mixture stirred and heated to reflux under nitrogen. After 2 hours the mixture is cooled, then stripped of methanol under reduced pressure. The residue is acidified with oxalic acid and the precipitate is filtered off, rinsed well with warm water, and dried to afford the pure product (2.6 g); mp 76° C. (dec).

EXAMPLE 112

4,5-Dibromo-3-(1-methylethoxy)-1-(phenylmethyl)-1H-pyrrole-2-carboxylic acid.

Ethyl 4,5-dibromo-3-(1-methylethoxy)-1-(phenylmethyl)-1H-pyrrole-2-carboxylate (2.5 g, 0.006 moles) is dissolved in methanol (30 mL), and 2N NaOH (15 mL) is added. The mixture is heated under nitrogen to reflux. After 1 hour the mixture is stirred into ice water (350 mL) and acidified with phosphoric acid. The precipitate is filtered off, rinsed with cold dilute acid, ice water and dried to afford the pure product (2.2 g); mp 122° C. (dec).

EXAMPLE 113

4,5-Dibromo-3-(1-methylethoxy)-1-methyl-1H-pyrrole-2-carboxylic acid.

Prepared by the method described in Example 111 from ethyl 4,5-dibromo-3-(1-methylethoxy)-1-methyl-1H-pyrrole-2-carboxylate (5.0 g, 0.014 moles) to give the product (4.6 g); mp 89° C. (dec).

EXAMPLE 114

4,5-Dibromo-3-(1-methylethoxy)-1H-pyrrole-2-carboxylic acid.

Methyl 4,5-dibromo-3-(1-methylethoxy)-1H-pyrrole-2-carboxylate (1.5 g, 0.004 moles) is stirred under nitrogen in DMSO (100 mL) at room temperature. Potassium tert-butoxide (2.5 g, 0.022 moles) is added. After 12 hours the mixture is stirred into water (600 mL) and extracted with ether twice. The ether extracts are discarded, and the aqueous phase is acidified with $H_3PO_4$, then extracted with $CH_2Cl_2$ (3x). The combined extracts are washed with brine and dried over $MgSO_4$. Removal of the solvent under reduced pressure left the product as a clear oil (1.4 g), sufficiently pure for further use.

EXAMPLE 115

4,5-Dibromo-3-(1-methylethoxy)-1-phenyl-N-1H-tetrazol-5-yl-1H-pyrrole-2-carboxamide.

A solution of 4,5-dibromo-3-(1-methylethoxy)-1-phenyl-1H-pyrrole-2-carboxylic acid (2.0 g, 0.005 moles) and 1,1'-carbonyldiimidazole (0.8 g, 0.005 moles) in THF (25 mL) is heated under argon to reflux. After 1 hour, 5-aminotetrazole (0.4 g, 0.005 moles) is added. After 2.5 hours, the mixture is stirred into ice water (250 mL) and acidified with dilute HCl. The precipitate is filtered off, rinsed with water and dried. Recrystallization from methyl t-butyl ether gave the pure product (0.8 g); mp 184° C. (dec).

EXAMPLE 116

4,5-Dibromo-3-(1-methylethoxy)-1-(phenylmethyl)-N-1H-tetrazol-5-yl-1H-pyrrole-2-carboxamide.

Prepared by the method described in Example 115 from 4,5-dibromo-3-(1-methylethoxy)-1-(phenylmethyl)-1H-pyrrole-2-carboxylic acid (2.1 g, 0.005 moles), 1,1'-carbonyldiimidazole (0.9 g, 0.0055 moles), and 5-aminotetrazole (0.43 g, 0.005 moles). Recrystallization from acetonitrile gave the product (1.2 g); mp 199°–205° C.

EXAMPLE 117

4,5-Dibromo-3-(1-methylethoxy)-1-methyl-N-1H-tetrazol-5-yl-1H-pyrrole-2-carboxamide.

Prepared by the method described in Example 115 from 4,5-dibromo-3-(1-methylethoxy)-1-methyl-1H-pyrrole-2-carboxylic acid (3.5 g, 0.01 moles), 1,1'-carbonyldiimidazole (1.7 g, 0.01 moles), and 5-aminotetrazole (0.87 g, 0.01 moles). Recrystallization from ethyl acetate gave the product (2.1 g); mp 218°–220° C. (dec).

EXAMPLE 118

4,5-Dibromo-3-(1-methylethoxy)-N-1H-tetrazol-5-yl-1H-pyrrole-2-carboxamide.

Prepared by the method described in Example 115 from 4,5-dibromo-3-(1-methylethoxy)-1H-pyrrole-2-carboxylic acid (1.4 g, 0.004 moles), 1,1'-carbonyldiimidazole (1.2 g, 0.007 moles), and 5-aminotetrazole (0.6 g, 0.007 moles). Recrystallization from acetonitrile gave the product (0.3 g); mp 194°–196° C.

EXAMPLE 119

3,4-Diisopropoxy-2,5-furandicarboxylic acid.

A solution of 1.25 g (11.11 mmol, 1.08 equiv) of potassium tert-butoxide in 7 mL of dimethyl sulfoxide is added rapidly to a room temperature solution of 1.26 g (5.16 mmol) of diethyl 3,4-dihydroxy-2,5-furandicarboxylate (Johnson, T. B. and Johns, C. O., *J. Am. Chem. Soc.*, 28, 489 (1906)) in 10 mL of dimethyl sulfoxide under a nitrogen atmosphere. The resulting solution is stirred at room temperature for 5 minutes and treated with 3.28 g (26.63 mmol, 5.16 equiv) of 2-bromopropane. The resulting reaction mixture is stirred for 24 hours at room temperature under a nitrogen atmosphere and poured onto water. The aqueous mixture is extracted with ethyl acetate (3x). The combined extracts are washed with water (2x) and saturated aqueous sodium chloride, dried over sodium sulfate and concentrated in vacuo to give 1.23 g of diethyl 3,4-diisopropoxy-2,5-furandicarboxylate as a solid.

The 1.23 g of the solid described above is dissolved in 10 mL of tetrahydrofuran and 3.5 mL of methanol and treated with 3.3 mL (8.3 mmol) of 2.5N sodium hydroxide in water. The resulting mixture is stirred at room temperature for 19 hours and extracted with diethyl ether (2x). The aqueous solution is acidified with aqueous 5% hydrochloric acid and the acidic solution is extracted with ethyl acetate (3x). The combined ethyl acetate extracts are washed with saturated aqueous sodium chloride, dried over sodium sulfate and concentrated in vacuo to give 1.00 g (1.02 g theo., 98%) of the desired product as a yellow solid. A sample triturated with hot diethyl ether was analytically pure; mp 131°–132° C.

EXAMPLE 120

3,4-Diisopropoxy-N,N'-di-1H-tetrazol-5-yl-2,5-furandicarboxamide.

A mixture of 0.80 g (2.94 mmol) of 3,4-diisopropoxy-2,5-furandicarboxylic acid and 1.10 g (6.78 mmol, 1.15 equiv) of 1,1'-carbonyl diimidazole in 20 mL acetonitrile under a nitrogen atmosphere is warmed at reflux for 1 hour. Triethylamine (1.45 g, 14.34 mmol, 2.43 equiv) and 0.58 g (6.82 mmol, 1.16 equiv) of anhydrous 5-aminotetrazole is added to the cooled reaction mixture and the resulting mixture is warmed at reflux under nitrogen for 16 hours. The cooled reaction mixture is poured onto 200 mL of ice water and the aqueous solution is acidified with 10% aqueous hydrochloric acid. The resulting precipitate is isolated by vacuum filtration, washed with water, triturated twice with hot acetonitrile to give 0.33 g 1.19 g theo., 28%) of analytically pure desired product containing 0.5 mol of 2-propanol; mp 256°–259° C. (dec).

EXAMPLE 121

5-Methyl-3,4-diisopropoxy-N-1H-tetrazol-5-yl-2-furancarboxamide.

Following the procedure described in Example 119, potassium tert-butoxide (7.1 g, 63.3 mmol, 1.2 equiv) and 2-bromopropane (32.8 g, 266.2 mmol, 10.1 equiv) in dimethyl sulfoxide (105 mL, 29 hours) are used to convert ethyl 3,4-dihydroxy-5-methyl-2-furancarboxylate (Cohen, A. M., U.S. Pat. No. 4,127,592, 1978) (4.5 g, 26.4 mmol) to ethyl 5-methyl-3,4-diisopropoxy-2-furancarboxylate. Flash chromatography (SiO$_2$, 3.5 × 13 cm, 25% ethyl acetate/hexane eluant) of the crude residue afforded 3.4 g (6.7 g theo., 51%) of the product as a yellow oil.

Following the procedure described in Example 119, saponification of the above oil (3.2 g, 12.6 mmol) with 2.5N aqueous sodium hydroxide (10.0 mL, 25.0 mmol, 2.0 equiv) in a refluxing mixture (22 hours) of tetrahydrofuran (30 mL), methanol (15 mL) and water (7 mL) afforded 2.8 g (2.85 g theo., 98%) of crude 5-methyl-3,4-diisopropoxy-2-furancarboxylic acid as an orange oil.

Following the procedure described in Example 120, 2.00 g (8.84 mmol) of the above carboxylic acid, 1.65 g (10.18 mmol, 1.15 equiv) of 1,1'-carbonyl diimidazole, 2.2 g (21.5 mmol, 2.4 equiv) of triethylamine, and 0.89 g (10.46 mmol, 1.18 equiv) of 5-aminotetrazole in refluxing (2.5 hours) acetonitrile (46 mL) is converted to the carbamoyltetrazole. Recrystallization from toluene afforded 0.75 g (2.73 g theo., 27%) of 5-methyl-3,4-diisopropoxy-N-1H-tetrazol-5-yl-2-furancarboxamide; mp 190°–192° C. (dec).

EXAMPLE 122

Methyl 3,4-dihydroxy-5-phenyl-2-furancarboxylate.

A solution of 18.0 g (108.0 mmol) of methyl DL-mandelate in 28 mL of tetrahydrofuran is added dropwise (30 minutes) to a mechanically stirred, 0° C. slurry of 5.5 g (138.0 mmol, 1.28 equiv) of 60% sodium hydride/mineral oil suspension in 195 mL of tetrahydrofuran under a nitrogen atmosphere. The resulting mixture is stirred at 0° C. for 30 minutes and treated dropwise (15 minutes) with 20.4 g (129.0 mmol, 1.19 equiv) of methyl bromoacetate. Sodium iodide (1.1 g, 7.0 mmol, 0.06 equiv) is added to the reaction mixture and the resulting mixture is stirred at room temperature for 4 hours. The reaction is poured onto 500 mL of saturated aqueous ammonium chloride, the layers were separated and the aqueous layer is extracted with ethyl acetate (4x). The combined organic extracts are dried over sodium sulfate and concentrated in vacuo to give an oil. Fractional distillation gave 16.0 g (25.7 g theo., 62%) of the dimethyl 2-phenyl diglycolate:bp 110°–125° C. (0.4 mm Hg) (preparation of diethyl 2-phenyl diglycolate is described in Solladie-Cavallo, A. and Vieles, P., *Bull. Soc. Chim. Fr.*, 517 (1967)).

Following a procedure analogous to the conversion of diethyl 2-methyl diglycolate to diethyl 3,4-dihydroxy-5-methyl-2-furandicarboxylate (Cohen, A. M., U.S. Pat. No. 4,127,592, 1978), dimethyl 2-phenyl diglycolate (9.0 g, 37.8 mmol), dimethyl oxalate (8.9 g, 75.4 mmol, 2.0 equiv), sodium methoxide (76.5 mmol, 2.0 equiv) in toluene (70 mL) is converted to 4.2 g (8.9 g theo., 47%) of methyl 3,4-dihydroxy-5-phenyl-2-furancarboxylate as a yellow solid. A sample of the furancarboxylate was recrystallized from toluene to afford an analytically pure sample; mp 195°–196° C.

EXAMPLE 123

3,4-Diisopropoxy-5-phenyl-N-1H-tetrazol-5-yl-2-furancarboxamide.

Following the procedure described in Example 119, methyl 3,4-dihydroxy-5-phenyl-2-furancarboxylate (4.80 g, 21.6 mmol is treated with potassium tert-butoxide (5.85 g, 52.3 mmol, 1.21 equiv) and 2-bromopropane (21.0 g, 170.4 mmol, 3.94 equiv) in dimethyl sulfoxide (70 mL) at room temperature for 6.5 hours to give 5.62 g of crude methyl 3,4-diisopropoxy-5-phenyl-2-furancarboxylate as a red oil.

Following the procedure described in Example 119, saponification of the above oil (5.32 g) with 2.5N aqueous sodium hydroxide (8.0 mL, 20 mmol) in refluxing (7 hours) methanol (55 mL) afforded 4.63 g of crude 3,4-diisopropoxy-5-phenyl-2-furancarboxylic acid as a red solid.

Following the procedure described in Example 120, the above crude carboxylic acid (4.63 g) is treated with 1,1'-carbonyl diimidazole (2.98 g, 18.4 mmol), triethylamine (5.1 g, 50.4 mmol) and 5-aminotetrazole (1.55 g, 18.2 mmol) in refluxing (4.5 hours) acetonitrile (60 mL) to give 4.74 g of the crude carbamoyltetrazole. Recrystallization from ethanol/water afforded 3.5 g (5.65 g theo., 62% from the carboxylic acid) of 3,4-diisopropoxy-5-phenyl-N-1H-tetrazol-5-yl-2-furancarboxamide as a tan solid; mp 122°–125° C. (dec).

EXAMPLE 124

5-Methyl-3-isopropoxy-N-1H-tetrazol-5-yl-2-furancarboxamide.

A solution of 1.6 g (14.3 mmol, 1.2 equiv) of potassium tert-butoxide in 11 mL of dimethyl sulfoxide is added to a solution of 2.0 g (11.8 mmol) of ethyl 3-hydroxy-5-methyl-2-furancarboxylate (Takei, H. and Mukaiyama, T., *Bull. Soc. Chem. Jpn.*, 43, 3607 (1970)) in 40 mL of dimethyl sulfoxide under a nitrogen atmosphere. The resulting solution is stirred at room temperature for 1 hour and treated with 5.9 g (47.9 mmol, 4.1 equiv) of 2-bromopropane. The reaction is stirred at room temperature for 7.5 hours under nitrogen and poured onto 100 mL of water. The aqueous solution is extracted with ethyl acetate (4x). The combined extracts are washed with water (2x) and saturated aqueous sodium chloride, dried over sodium sulfate and concentrated in vacuo to give 1.7 g (2.5 g theo., 68%) of ethyl 5-methyl-3-isopropoxy-2-furancarboxylate as a pale, yellow oil.

Saponification of 1.0 g (5.0 mmol) of the above oil, as described in Example 119, using 4.0 mL (10.0 mmol, 2.0 equiv) of 2.5N aqueous sodium hydroxide in refluxing (7.5 hours) methanol (100 mL) gave 0.61 g of the unstable 5-methyl-3-isopropoxy-2-furancarboxylic acid as a yellow solid.

Following the procedure described in Example 120, 0.60 g (3.7 mmol, 1.1 equiv) of 1,1'-carbonyl diimidazole, 0.33 g (3.9 mmol, 1.2 equiv) of 5-aminotetrazole and 0.80 g (7.9 mmol, 2.4 equiv) of triethylamine in refluxing (16 hours) acetonitrile (15 mL) are used to convert 0.61 g (3.3 mmol) of the carboxylic acid described above to 0.45 g of the carbamoyltetrazole as a tan solid. Recrystallization gave 0.35 g (1.26 g theo., 28% overall) of analytically pure 5-methyl-3-isopropoxy-N-1H-tetrazol-5-yl-2-furancarboxamide as a tan, crystalline solid; mp 240°–242° C. (dec).

EXAMPLE 125

N-1H-Tetrazol-5-yl-2-furancarboxamide.

Following the procedure described in Example 120, 2-furancarboxylic acid (5.00 g, 44.46 mmol) is treated with 1,1'-carbonyl diimidazole (8.31 g, 51.25 mmol, 1.15 equiv), triethylamine (10.9 g, 107.6 mmol, 2.4 equiv) and 5-aminotetrazole (4.51 g, 53.02 mmol, 1.19 equiv) in refluxing (17 hours) acetonitrile (250 mL) to give the crude carbamoyl product. Recrystallization from N,N-dimethyl formamide/water afforded 4.90 g (7.96 g theo., 62%) of N-1H-tetrazol-5-yl-2-furancarboxamide as a white solid; mp 280°–283° C. (dec).

EXAMPLE 126

5-Trimethylsilyl-N-1H-tetrazol-5-yl-2-furancarboxamide.

Following the procedure described in Example 120, 5-trimethylsilyl-2-furancarboxylic acid (Knight, D. W. and Nott, A. P., *J. Chem. Soc., Perkin Trans.* 1, 26, 1125 (1985)) (5.00 g, 27.13 mmol) is treated with 1,1'-carbonyl diimidazole (5.13 g, 31.64 mmol, 1.17 equiv), triethylamine (6.6 g, 65.3 mmol, 2.4 equiv) and 5-aminotetrazole (2.76 g, 32.44 mmol, 1.20 equiv) in refluxing (21 hours) acetonitrile (130 mL) to give 6.75 of crude carbamoyltetrazole. Recrystallization from isopropanol afforded 3.75 g (6.82 g theo., 55%) of analytically pure 5-trimethylsilyl-N-1H-tetrazol-5-yl-2-furancarboxamide as a white solid; mp 247°–248° C.

EXAMPLE 127

3-Isopropylthio-5-trimethylsilyl-2-furancarboxylic acid.

A solution of 25.01 g (136.0 mmol) of 5-trimethylsilyl-2-furancarboxylic acid (Carpenter, A. J. and Chadwick, D. J., *Tetrahedron Lett.*, 26, 1777 (1985)) in 50 mL of dry tetrahydrofuran is added over 10 minutes to a −76° C. solution of freshly generated lithium diisopropylamide (328.0 mmol, 2.41 equiv) in dry tetrahydrofuran (175 mL) under nitrogen atmosphere and the resulting mixture is stirred at −76° to 65° C. for 1.5 hours. The reaction is recooled to −76° C. and treated with 23.58 g (151.0 mmol, 1.11 equiv) of diisopropyl sulfide in 25 mL of tetrahydrofuran and the resulting mixture is stirred for 4 hours while slowly warming to room temperature. The reaction is poured onto 1.5 L of water and the aqueous mixture is extracted with diethyl ether (200 mL, 3x), treated with 400 g of ice, and acidified with concentrated hydrochloric acid. The resulting precipitate is collected by vacuum filtration and recrystallized from diethyl ether/cyclohexane to give 18.22 g (35.14 g theo., 52%) of analytically pure 3-isopropylthio-5-trimethylsilyl-2-furancarboxylic acid as a tan solid; mp 181°–183° C.

EXAMPLE 128

3-Isopropylthio-5-trimethylsilyl-N-1H-tetrazol-5-yl-2-furancarboxamide.

Following the procedure described in Example 120, 3-isopropyl-5-trimethylsilyl-2-furancarboxylic acid (4.00 g, 15.48 mmol) is treated with 1,1'-carbonyl diimidazole (3.00 g, 18.50 mmol, 1.20 equiv), triethylamine (3.8 g, 37.3 mmol, 2.4 equiv) and 5-aminotetrazole (1.59 g, 18.69 mmol, 1.21 equiv) in refluxing (1.5 hours) acetonitrile (74 mL) to give the crude carbamoyltetrazole. Recrystallization from toluene afforded 3.64 g (5.04 g theo., 72%) of analytically pure 3-isopropylthio-5-trimethylsilyl-N-1H-tetrazol-5-yl-2-furancarboxamide as a tan solid; mp 181°–182° C.

EXAMPLE 129

3-Isopropylthio-N-1H-tetrazol-5-yl-2-furancarboxamide.

A solution of 5.0 mL (5.0 mmol, 1.1 equiv) of 1.0 M tetra-n-butylammonium fluoride/tetrahydrofuran is added to a room temperature solution of 1.51 g (4.64 mmol) of 3-isopropylthio-5-trimethylsilyl-N-1H-tetrazol-5-yl-2-furancarboxamide in 15 mL of tetrahydrofuran. The resulting mixture is stirred at room temperature for 18 hours and concentrated in vacuo. The residue is suspended in water (100 mL) and acidified with 10% aqueous hydrochloric acid. The precipitate is isolated by vacuum filtration and recrystallized from toluene affording 1.26 g (1.77 g theo., 71%) of the carbamoyltetrazole as a tan solid; mp 201°–203° C.

EXAMPLE 130

5-Bromo-3-isopropylthio-N-1H-tetrazol-5-yl-2-furancarboxamide.

A solution of 3.1 g (19.5 mmol, 1.6 equiv) of bromine in 7 mL of chloroform is added dropwise to a room temperature solution of 3.98 g (12.22 mmol) of 3-isopropylthio-5-trimethylsilyl-N-1H-tetrazol-5-yl-2-furancarboxamide in 13 mL of chloroform and 20 mL of glacial acetic acid under nitrogen atmosphere. The resulting mixture is stirred at room temperature for 23 hours then poured onto 200 mL of water. The aqueous mixture is extracted with ethyl acetate (3x). The combined extracts are washed with 10% aqueous sodium thiosulfate and saturated aqueous sodium chloride, dried over sodium sulfate and concentrated in vacuo to give a yellow solid. Recrystallization from isopropanol/water gave 1.58 g (4.06 g theo., 38%) of the desired product as a yellow solid; mp 200°–210° C. (dec).

EXAMPLE 131

2-(4,5-Dibromo-2-furanyl)-4,4-dimethyloxazoline.

Meyers' general approach to oxazoline synthesis was followed (Meyers, A. I.; Temple, D. T.; Haidukewych, D.; Mihelich, E. D.; *J. Org. Chem.*, 39, 2787 (1974)).

A mixture of 11.18 g (41.42 mmol) of 4,5-dibromo-2-furan carboxylic acid (Chadwick, D. J.; Chambers, J.; Meakins, G. D.; Snowden, R. L.; *J. Chem. Soc., Perkin Trans.* 1, 1766 (1972)) and 6.3 g (49.3 mmol, 1.2 equiv) of oxalyl chloride in $CH_2Cl_2$ (150 mL) is treated with 3 drops of DMF. Carbon dioxide immediately evolves from the reaction and is controlled with occasional cooling in an ice/$H_2O$ bath. The reaction is concentrated in vacuo after stirring for 2 hr. The residue is distilled under vacuum using a Kugelrohr apparatus affording 11.69 g of the acid chloride as a pale, yellow oil (the method of acid chloride formation is reported in: Burgstahler, A. W.; Weigel, L. O.; Shaefer, C. G.; *Synthesis* 767 (1976)).

A solution of the acid chloride (40.54 mmol) in $CH_2Cl_2$ (35 mL) is cooled to 0° C. and 7.22 g (81.08 mmol, 2.00 equiv) of 2-amino-2-methyl-1-propanol in $CH_2Cl_2$ (20 mL) is added dropwise. The reaction is stirred at 25° C. for 2.5 hr and the reaction is filtered. The filtrate is concentrated in vacuo. The precipitate from the filtration is washed with 10% aqueous HCl, $H_2O$, and diethyl ether. The washed precipitate is combined with the filtrate residue, the resulting mixture is suspended in toluene (100 mL), and cooled to 0° C. Thionyl chloride 14.4 g (120.6 mmol) in toluene (10 mL) is added dropwise to the 0° C. suspension. The reaction is stirred as 25° C. for 18 hr, concentrated in vacuo, taken up in $H_2O$ and made basic with aqueous 4N NaOH. The basic aqueous solution is extracted with diethyl ether (4X). The combined extracts are washed with saturated aqueous NaCl, dried ($Na_2SO_4$) and concentrated in vacuo to afford 9.91 g (13.38 g, theo.; 74%) of the desired oxazoline. Material is used as is without further purification.

EXAMPLE 132

2-(4,5-Dibromo-3-isopropylthio-2-furanyl)-4,4-dimethyloxazoline.

A solution of 9.63 g (29.81 mmol) of 2-(4,5-dibromo-2-furanyl)-4,4-dimethyloxazoline in dry tetrahydrofuran (30 mL) is added dropwise to a −78° C. solution of freshly generated lithium diisopropylamide (33.89 mmol, 1.14 equiv) in tetrahydrofuran (80 mL) under an argon atmosphere. The resulting solution is stirred at −78° C. for 10 min and a solution of 5.49 g (46.49 mmol, 1.56 equiv) of isopropyl sulfide in tetrahydrofuran (20 mL) is added dropwise to the reaction. The reaction is stirred for 3.75 hr at −78° to −10° C. and poured onto 5% aqueous HCl (350 mL). The resulting aqueous solution is extracted with diethyl ether (4X). The combined organic extracts are washed with aqueous saturated NaCl, dried ($Na_2SO_4$), and concentrated in vacuo. Flash chromatography ($SiO_2$, 7×25 cm, 10% $CH_2Cl_2$/10% ethyl acetate/hexane) affords 7.67 g (11.84 g theo.; 65%) of the desired product as a yellow solid. Recrystallization from hexane affords an analytical sample; mp 71°–72° C.

EXAMPLE 133

4,5-Dibromo-3-(isopropylthio)-2-furancarboxylic acid.

A mixture of 3.01 g (7.58 mmol) of 2-(4,5-dibromo-3-isopropylthio-2-furanyl)-4,4-dimethyloxazoline and aqueous 4N HCl is warmed at reflux under $N_2$ atmosphere for 0.5 hr. The reaction is cooled to 0° C. and treated with methanol (60 mL), tetrahydrofuran (30 mL), and 4.25 g (177.0 mmol) of anhydrous LiOH. The reaction is stirred at 0° C. for 2 hr and 25° C. for 16 hr, then concentrated in vacuo. The resulting residue is dissolved in $H_2O$ and extracted with diethyl ether (2X). The aqueous solution is acidified with aqueous 10% HCl and extracted with ethyl acetate (4X). The combined extracts are washed with aqueous saturated NaCl, dried ($Na_2SO_4$), and concentrated in vacuo to afford 1.63 g (2.61 g theo.; 62%) of the carboxylic acid as a beige solid. Recrystallization from diethyl ether/hexane affords an analytical sample; mp 130°–131° C.

EXAMPLE 134

4,5-Dibromo-3-(isopropylthio)-N-1H-tetrazol-5-yl-2-furancarboxamide.

Following the procedure described in Example 120, 1.90 g (5.69 mmol) of 4,5-dibromo-3-(isopropylthio)-2-furancarboxylic acid, 1.11 g (6.85 mmol, 1.20 equiv) of 1,1'-carbonyl diimidazole, 1.38 g (13.63 mmol, 2.40 equiv) of triethylamine, and 0.58 g (6.82 mmol, 1.20 equiv) of 5-aminotetrazole in refluxing (18 hr) acetonitrile (25 mL) affords the carbamoyl tetrazole. Recrystallization from ethyl acetate/hexane affords 1.43 g (2.34 g theo.; 61%) of an analytical sample; mp 241°–242° C.

EXAMPLE 335

Methyl 4-bromo-3-[(dimethylamino)thioxomethoxy]-5-methyl-2-thiophenecarboxylate.

Methyl 4-bromo-3-hydroxy-5-methyl-2-thiophenecarboxylate (2.5 g, 10 mmoles) is stirred under argon in DMF (20 mL). Dimethylthiocarbamyl chloride (2.65 g, 21 mmoles) and 1,4-diazabicyclo[2.2.2]octane (2.4 g, 21 mmoles) are added. The mixture is stirred at room temperature for 2 hours, then at 50° C. for 20 hours, then poured into ice water (200 mL) and extracted twice with toluene. The combined extracts are washed successively with 2N HCl, water, 0.5 M $NaHCO_3$, and water, then dried over $MgSO_4$. Removal of the solvent under reduced pressure, followed by recrystallization from ethyl acetate affords the product (2.7 g); mp 152°–154° C.

EXAMPLE 136

Methyl 4-bromo-3-{[(dimethylamino)carbonyl]thio}-5-methyl-2-thiophenecarboxylate.

Methyl 4-bromo-3-[(dimethylamino)thioxomethoxy]-5-methyl-2-thiophenecarboxylate (4.3 g, 13 mmoles) is stirred under argon in dipheyl ether (50 mL) and heated to 225° C. After 2.5 hours the mixture is allowed to cool and is then stirred into diethyl ether (250 mL). After 45 minutes the precipitate is filtered off, rinsed with diethyl ether and dried to afford the product (2.8 g); mp 175°–176° C.

EXAMPLE 137

4-Bromo-3-mercapto-5-methyl-2-thiophenecarboxylic acid.

Methyl 4-bromo-3-{[(dimethylamino)carbonyl]thio}-5-methyl-2-thiophenecarboxylate (1.5 g, 4 mmoles) is stirred in a mixture of methanol (3 mL) and 5N sodium hydroxide (10 mL) and heated under reflux. After 2½ hours the mixture is cooled, stirred into ice water, and acidified with concentrated HCl. The precipitate is filtered off, rinsed with water and dried to afford the product (1.0 g); mp 177° C. (dec).

EXAMPLE 138

1-Methyl ethyl 4-bromo-5-methyl-3-[(1-methylethyl)thio]-2-thiophenecarboxylic acid.

4-Bromo-3-mercapto-5-methyl-2-thiopenecarboxylic acid (9.0 g, 36 mmoles) is stirred under argon in acetonitrile (100 mL). Triisopropylisourea (26.5 g, 142 mmoles) is added and the mixture heated under reflux. After 18 hours the mixture is cooled, the solvent is removed by rotary evaporator, and the residue mixed with ether (100 mL) and cooled. The precipitate is filtered off and rinsed with cold ether, then discarded. The filtrate is stripped of ether by rotary evaporator, and the excess triisopropylisourea is removed by distillation under reduced pressure (bp 80° C., 10 mm) to leave the product (11.1 g) as an oil sufficiently pure for further use.

EXAMPLE 139

4-Bromo-5-methyl-3-[(1-methylethyl)thio]-2-thiophenecarboxylic acid.

1-Methylethyl 4-bromo-5-methyl-3-[(1-methylethyl)thio]-2-thiophenecarboxylate (11.1 g, 33 mmoles) is stirred under argon in a mixture of methanol (10 mL) and 1N sodium hydroxide (70 mL), and heated under reflux. After 4.5 hours the mixture is cooled, stirred into ice water (300 mL) and extracted twice with ether (50 mL). The aqueous layer is acidified with concentrated HCl and the precipitate is filtered off, rinsed with water and dried to afford the product (8.4 g); mp 132°–134° C.

EXAMPLE 140

4-Bromo-5-methyl-3-[(1-methylethyl)thio ]-N-1H-tetrazol-5-yl-thiophene-2-carboxamide.

A mixture of 4-bromo-5-methyl-3-[(1-methylethyl)thio]-2-thiophenecarboxylic acid (3.0 g, 10 mmoles) and 1,1'-carbonyldiimidazole (1.8 g, 11 mmoles) in THF (25 mL) is stirred under argon and heated under reflux. After 1.5 hours 5-aminotetrazole (0.87 g, 10 mmol) is added and heating continued for an additional 2.5 hours. The mixture is then cooled, stirred into ice water (300 mL) and acidified with concentrated HCl. The precipitate is filtered off, washed with 4N HCl, rinsed with water and dried to afford the product (3.5 g); mp 235° C. (dec).

The usefulness of the compounds of the present invention as inhibitors of histamine release is demonstrated by the following tests. The tests are essentially as generally accepted among the ordinarily skilled artisans to show activity having usefulness to treat the diseases or conditions as set out in the present invention. A description of each procedure follows.

HISTAMINE RELEASE FROM HUMAN BASOPHILS (hereinafter HHB)

The HHB assay quantitates active histamine release, and its inhibition by drugs, from basophils of human blood. Thus, the assay provides evaluation of the compounds of formula I for treating the conditions or diseases as is the present invention. As described herein the assay includes modifications of the method described by R. P. Siroganian in "An Automated Continuous-Flow System for the Extraction and Fluorometric Analysis of Histamine", *Anal. Biochem.*, 57, 383–394 (1974).

METHODS
Preparation of Leukocytes

Seventy mL of blood are drawn from allergic donors (chosen on the basis of adequate histamine induced by a challenge), using standard venipuncture methods, into 10 mL Vacutainers with 0.08 mL/tube 15% EDTA in water as anticoagulant. The blood samples are placed briefly on a rotary mixer. All glassware contacting the blood is siliconized. The blood is aliquoted into three plastic 50 mL centrifuge tubes and the volume is noted. Hespan (hydroxy ethyl starch), 0.5 mL per 1.0 mL of blood, is added. The tubes are inverted several times to mix and are left undisturbed at room temperature until a sharp separation is observed between the settled red cells and the leukocyte and platelet-rich plasma. This usually occurs within 35–45 minutes.

The plasma fraction is pipetted off and placed into two clean plastic 50 mL centrifuge tubes. The tubes are centrifuged for 12 minutes at 4° C. in a Sorval RC-3 centrifuge with an HL-8 rotor at 1050 RPM (100 g). The platelets remain in the plasma and are discarded. The pelleted leukocytes are shaken gently to disrupt the cell button and washed twice as described:

Wash 1. Five mL of HA buffer with 0.005 M EDTA is added to the dispersed cells in each tube and gently vortexed. 25 mL of buffer is then added and gently vortexed. The samples are again centrifuged as described earlier. The supernatant is poured off, and the cell button in each tube is gently dispersed.

Wash 2. Five mL of HA buffer with EDTA is added to each tube to resuspend the cells. Leukocytes are then pooled into one tube and the volume is brought up to 40 mL with HA buffer with EDTA and gently vortexed. The pooled sample is centrifuged at 1050 RPM for 12 minutes. The supernatant fluid is discarded and the cell button is dispersed. Sixteen mL of HACM buffer (Appendix 3) is added to the washed cells and gently vortexed. A sample is prepared for Hematology, where a total white blood cell and platelet count is done using a Coulter Counter.

Aliquots (0.1 mL) of cells are added to assay tubes containing 0.4 mL of either 6% perchloric acid (for total histamine content), vehicle control (for spontaneous release), or drug. The tubes are incubated at room temperature for 8 minutes, and then placed in a 37° C. water bath for two more minutes. Buffer or challenge agents (at 37° C.) are added to the tubes and they are incubated for an additional 45 minutes at 37° C. The tubes are then spun at 2000 RPM (1200 g) for 3 minutes to pellet the cells and the supernatants are poured into assay cups.

Drug Preparation

A 300 μM stock solution of each test compound is prepared as follows: an appropriate amount of compound (molecular weight/33.33) is weighed out into a 100 mL volumetric flask and 0.5 mL DMSO is added. If the compound does not dissolve readily, it is warmed gently on a hot plate and approximately 30 mL of distilled water is added. If the compound is in solution, distilled water is used to bring it up to 100 mL total volume. If the drug is not in solution, 0.2 mL 1N NaOH (or HCl) is added, and then distilled water is added to yield 100 mL total solution. Five mL of the stock solution is diluted (1:2) with 5 mL of two times concentrated HACM buffer to yield the stock working concentration of 150 μM. When added to the cells and stimulus, a final test concentration of 100 μM drug results (400 μL drug, 100 μL cells and 100 μL challenge agent or vehicle). Further dilutions are made with HACM buffer for 33, 10, 3.3, 1.0 μM, etc.

Challenge Agent Preparation

Short ragweed and house dust extracts (Greer Laboratories, Inc.) are supplied as aqueous extracts in stock concentrations of 40,000 and 10,000 protein nitrogen units per milliliter (PNU/mL), respectively. Aqueous solutions of anti-IgE antisera (rabbit-raised antibody) are purchased from Dako via Accurate Chemicals. The tripeptide f-met-leu-phe from Vega Biochemicals is used. The aqueous solutions of ragweed, house dust, and anti-IgE are diluted 1:2 with two times concentrated HACM and then further diluted with HACM to yield final stock concentrations of 6000 PNU/mL for ragweed and house dust, and a 1:50 dilution for the anti-IgE antisera. For fmlp, 28.5 mg of the tripeptide is dissolved in 1 mL of DMSO or 1 mL glacial acetic acid, then 49 mL distilled water and 50 mL of two times HACM are added to yield a final stock of 600 μM in HACM. The pH is adjusted to 7.4. Further dilutions for working solutions are made in HACM buffer. All stock and working solutions are stored at 4° C. Working solutions comprise 1/6 of the final volume in the cell reaction, therefore, working solutions of challenge agents are made up six times the required final concentration (i.e., 600 μM f-met-leu-phe yields 100 μM final concentration in the cellular reaction).

Protocol Design

Samples are run in triplicate, using either 1.5 mL polypropylene-capped reaction tubes, or 5.0 mL plastic uncapped tubes. Test compounds and challenge agents are prepared in HACM buffer, as described above. Fixed volume pipettes are used. A sample protocol showing volumes used and the timing of reagent additions is in Appendix 2.

Test compound or vehicle control is added to three reaction tubes at 1.5x the final desired concentration (i.e., 400 μL of test compound per 600 μL total reaction volume). One hundred μL of cells is added to each tube and the mixture is incubated for eight minutes at room temperature, and two minutes at 37° C. before antigen or other stimulus challenge. One hundred μL of the challenge agent at 6x the final concentration is then added, and the final mixture is incubated at 37° C. for 45 minutes in a shaking water bath. This ensures that the cell preparation is constantly in suspension. The reaction is stopped by centrifugation at 2000 RPM for three minutes at 4° C. The supernate ($\approx$500 μL) is poured into 2.0 mL autoanalyzer beakers and assayed for histamine by the fluorometric method.

In each experiment, cells from one donor are challenged with one or more of the challenge agents, according to the designed protocol and the previously determined sensitivity of the donor to particular challenge agents. Short ragweed and house dust concentrations are expressed in PNU/mL, fmlp challenges are in micromolar concentration (μM, and anti-IgE antisera and C5a challenges are in dilutions, e.g., IE-5 (1:100,000), 3E-5 (1:30,000), and 1E-4 (1:10,000).

Calculation and Interpretation of Results

The total histamine concentration in the "total" (acid-treated) samples must be 15 ng/mL to be acceptable. Spontaneous release of histamine from the cells should not exceed 15% of the total histamine, and is frequently <5%. The maximum percentage histamine released varies with the donor. The net amount released by the challenge agent must exceed 25% of the total cellular histamine to confidently assess inhibition by test compounds. Spontaneous histamine release is subtracted from both "totals" and challenged cells to calculate net percent release. Percent inhibition is calculated using the following formula:

$$1 - \left[ \frac{\text{Mean net \% release treated samples}}{\text{Mean net \% release for challenged control}} \right] \times 100 = \text{\% inhibition}$$

FRAGMENTED LUNG ANAPHYLAXIS TEST (hereinafter FLAT)

The FLAT assay quantitates histamine release, and its inhibition by drugs, from actively sensitized guinea pig lung. Thus, the assay also provides evaluation of compounds of formula I for treating conditions or diseases as is the present invention. The histamine concentration is quantitated using a fluorometric method as originally described by Shore et al., "A Method for the Fluorometric Assay of Histamine in Tissues", JPEt, 127, 182 (1959) and using automated methods as modified by Siraganian cited above.

METHODS

The lungs from guinea pigs sensitized to ovalbumin (OA) are excised and chopped into small pieces. They are incubated in a 37° C. water bath and are exposed to the antigen in the presence of drug or vehicle. Histamine (together with a variety of enzymes and other organic compounds) is released from the granules of the mast cells within the tissue fragments when challenged with antigen. Since the symptoms of asthma and hay fever apparently result from the activation of these mast cells, histamine release is a marker of that activation. Drug effect is measured as the inhibition of histamine release. Histamine release is quantitated by an automated fluorometric method using a series of continuous flow extraction steps. At the end of the extraction procedure histamine is coupled with o-phthalaldehyde to form a condensation product which fluoresces. The fluorescence intensity correlates linearly with the histamine concentration.

Inhibition of Histamine Release

Compounds to be tested are dissolved in 0.5 mL of DMSO. H$_2$O is added to this solution to form a final drug concentration of $2 \times 10^{-4}$ M in 0.5% DMSO (final incubation concentration 0.25%). Compounds insoluble in this solution are solubilized by adding 100–200 μL of 1N NaOH. Two mL of drug or vehicle control is combined with 0.6 mL of a 4.4 times HEPES-Ca-Mg-buffer concentrate to maintain the correct buffer molarity and pH. Either drug or vehicle solution (2.6 mL) is added to vials containing the tissue fragments in 1 mL of HEPES-Ca-Mg-buffer, for a volume of 3.6 mL.

Several test groups are run in each experiment. They are: (1) spontaneous histamine release (receiving the drug vehicle and buffer only), (2) OA-induced (control) histamine release (receiving drug vehicle and OA), (3) OA-induced histamine release in the presence of a test compound, and (4) spontaneous histamine release in the presence of test compound and buffer.

Ten minutes after drug addition, 0.4 mL of 3 mg/mL OA in buffer or buffer alone is added to each vial (final bath concentration of 0.3 mg/mL OA) and incubated 15 minutes at 37° C. One mL of supernatant (incubate) is then removed from each vial for histamine assay. Histamine remaining in the tissue fragments is released by adding 5 mL of 8% perchloric acid to the vials, incubating ten minutes after which an additional 2 mL (total) is removed for histamine assay. The histamine-containing samples, both "incubate" and "total", are centrifuged for 12 minutes at 1200×g on a Sorvall centrifuge and 0.7 mL is removed from each tube for histamine determination. In this method histamine is extracted using a series of continuous flow steps as described in HHB assay above. At the end of the extraction procedure histamine is coupled with o-phthalaldehyde at pH 12 to form a condensation product which fluoresces when excited by 450 nm wavelength light. The relative fluorescence output at which peak readings are proportional to the concentration of histamine are used to calculate the percent inhibition of antigen induced histamine.

Using the HHB assay the compounds of Examples 71, 75, 78, 81, 82, 83, 84, 85, 87, 89, 90, 93, 94, 95, 98 and 117 are found to be among the preferred compounds by inhibition of the release of histamine from human basophils challenged with antigen.

Further, more particularly, the invention compounds of the noted examples are found to inhibit release of histamine from sensitized guinea pig lungs in the FLAT assay as shown in the following Table A.

TABLE A

| Example No. | Concentrations ($\mu$M) Giving 60-80% Histamine Inhibition |
|---|---|
| 70 | 0.1 |
| 79 | 1.0 |
| 80 | 10 |
| 89 | 10 |
| 84 | 1.0 |
| 81 | 10 |
| 82 | 10 |
| 83 | 1.0 |
| 90 | 1.0 |
| 94 | 10 |
| 71 | 10 |
| 85 | 10 |
| 92 | 10 |
| 93 | 1.0 |
| 72 | 10 |
| 115 | 100 |
| 117 | 100 |
| 116 | |
| 118 | |
| 73 | 1.0 |
| 74 | 10 |
| 75 | 10 |
| 77 | 10 |
| 78 | 1.0 |
| 86 | 10 |
| 123 | 100 |
| 129 | 10 |
| 130 | 10 |
| 128 | 10 |
| 140 | 7.5 |

Accordingly, the present invention also includes a pharmaceutical composition for treating one of the above diseases or conditions comprising an antidisease or anticondition effective amount of a compound of the formula I as defined above together with a pharmaceutically acceptable carrier.

The present invention further includes a method for treating one of the above named diseases or conditions in mammals, including man, suffering therefrom comprising administering to such mammals either orally or parenterally, preferably oral, a corresponding pharmaceutical composition containing a compound of formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferaby to 1 to 50 mg according to the particular application and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. A process for preparing a compound of the formula (I')

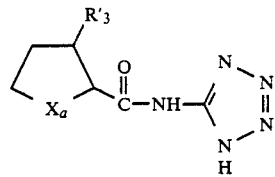

wherein $R'_3$ is OH and $X_a$ is NH or $NR_4$ by
(a) contacting a compound of the formula $HX_aCH_2CO_2R'_5$ wherein $X_a$ is as defined above and $R'_5$ is lower alkyl with methyl α-haloacrylate wherein halo is chloro or bromo and hydrolyzing the resulting product; and
(b) treating the product of (a) with 5-aminotetrazol in the presence of a coupling agent.

2. A process for the preparation of a compound of the formula (II')

wherein $R_3'$ is OH, $X_a$ is NH or $NR_4$ and $R_5$ is hydrogen or alkyl; which comprises contacting a compound of the formula $HX_aCH_2CO_2R_5'$ wherein $X_a$ is as defined above and $R_5'$ is lower alkyl with methyl α-haloacrylate wherein halo is chloro or bromo and then adding a base to obtain the compound of formula II'.

* * * * *